United States Patent
Stebbins et al.

(10) Patent No.: US 12,390,412 B2
(45) Date of Patent: Aug. 19, 2025

(54) HYDROGLYCOLIC COSMETIC COMPOSITION WITH A HIGH ACTIVE CONTENT

(71) Applicant: L'OREAL, Paris (FR)

(72) Inventors: Nicholas David Stebbins, Clark, NJ (US); Susan Halpern, Basking Ridge, NJ (US)

(73) Assignee: L'OREAL, Paris (FR)

( * ) Notice: Subject to any disclaimer, the term of this patent is extended or adjusted under 35 U.S.C. 154(b) by 191 days.

(21) Appl. No.: 17/125,942

(22) Filed: Dec. 17, 2020

(65) Prior Publication Data

US 2022/0192961 A1 Jun. 23, 2022

(51) Int. Cl.
| | | |
|---|---|---|
| A61K 8/73 | (2006.01) | |
| A61K 8/34 | (2006.01) | |
| A61K 8/36 | (2006.01) | |
| A61K 8/365 | (2006.01) | |
| A61K 8/368 | (2006.01) | |
| A61K 8/37 | (2006.01) | |
| A61K 8/41 | (2006.01) | |
| A61K 8/42 | (2006.01) | |
| A61K 8/44 | (2006.01) | |
| A61K 8/46 | (2006.01) | |
| A61K 8/49 | (2006.01) | |
| A61K 8/55 | (2006.01) | |
| A61K 8/60 | (2006.01) | |
| A61K 8/67 | (2006.01) | |
| A61Q 17/04 | (2006.01) | |

(52) U.S. Cl.
CPC .............. *A61K 8/735* (2013.01); *A61K 8/342* (2013.01); *A61K 8/345* (2013.01); *A61K 8/347* (2013.01); *A61K 8/36* (2013.01); *A61K 8/365* (2013.01); *A61K 8/368* (2013.01); *A61K 8/375* (2013.01); *A61K 8/41* (2013.01); *A61K 8/42* (2013.01); *A61K 8/44* (2013.01); *A61K 8/466* (2013.01); *A61K 8/4946* (2013.01); *A61K 8/55* (2013.01); *A61K 8/60* (2013.01); *A61K 8/676* (2013.01); *A61K 8/678* (2013.01); *A61Q 17/04* (2013.01); *A61K 2800/30* (2013.01); *A61K 2800/596* (2013.01)

(58) Field of Classification Search
CPC .......... A61K 8/342; A61K 8/55; A61K 8/678; A61K 8/4946; A61K 8/365; A61K 8/345; A61K 8/466; A61K 8/60; A61K 8/676; A61K 8/347; A61K 8/735; A61K 8/36; A61K 8/44; A61K 8/368; A61K 8/42; A61K 8/41; A61K 8/375; A61K 2800/596; A61K 2800/30; A61Q 17/04; A61Q 19/08

See application file for complete search history.

(56) References Cited

U.S. PATENT DOCUMENTS

| | | | |
|---|---|---|---|
| 5,140,043 A | 8/1992 | Darr et al. | |
| 7,179,841 B2 | 2/2007 | Zielinski et al. | |
| 9,248,082 B2 | 2/2016 | Pinnell et al. | |
| 2005/0154054 A1 | 7/2005 | Zielinski et al. | |
| 2005/0239749 A1* | 10/2005 | Kambayashi | A61P 17/00 424/70.13 |
| 2010/0202985 A1* | 8/2010 | SenGupta | A61K 8/27 424/59 |
| 2015/0190371 A1* | 7/2015 | Duprat | A61P 17/00 514/429 |
| 2017/0360691 A1* | 12/2017 | Dueva-Koganov | A61Q 19/08 |
| 2020/0222438 A1* | 7/2020 | Hammond | A61K 33/30 |
| 2021/0186838 A1* | 6/2021 | Siefken | A61Q 19/08 |
| 2021/0299032 A1* | 9/2021 | Bodnar | A61Q 19/007 |
| 2022/0202671 A1* | 6/2022 | Stebbins | A61K 8/735 |
| 2022/0211599 A1* | 7/2022 | Stebbins | A61K 8/365 |

FOREIGN PATENT DOCUMENTS

| | | |
|---|---|---|
| JP | 2013199498 A | 10/2013 |
| WO | WO 2021/089500 A1 * | 5/2021 |

OTHER PUBLICATIONS

PH of Organic Acids and Salts: https://www.aqion.de/site/ph-of-organic-acids. (Year: 2023).*
Simulgel 600 SDS: chrome-extension://efaidnbmnn-nibpcajpcglclefindmkaj/https://www.ulprospector.com/documents/1134639.pdf?bs=1432&b=46885&st=20&r=na&ind=personalcare. (Year: 2019).*
PCT Notification of Transmittal of the International Search Report and the Written Opinion of the International Searching Authority, or the Declaration issued to counterpart application No. PCT/IB2021/061876 dated Feb. 3, 2022.
Search Report issued to French counterpart application No. FR 2103314 dated Jan. 27, 2022.
Mintel, Anonymous, "V11 Total Care Serum" XP055881227, No. 4785217, www.gnpd.com.
Mintel, Anonymous, "C15 Super Booster" XP055881263, No. 7201459, www.gnpd.com.
Mintel, Anonymous, "Day Cream SPF 30" XP055881265, No. 7277485, www.gnpd.com.

(Continued)

*Primary Examiner* — Hong Yu
(74) *Attorney, Agent, or Firm* — McNees Wallace & Nurick LLC

(57) ABSTRACT

A hydroglycolic cosmetic composition includes at least one or a combination of skin actives comprising at least one of ascorbic acid, a cinnamic acid derivative, Vitamin E, or a combination of these, and a glycol or combination of glycols selected from the group consisting of: dipropylene glycol, pentylene glycol, hexylene glycol, a combination of dipropylene glycol and pentylene glycol, and a combination of dipropylene glycol and hexylene glycol. The composition demonstrates stability of solubility of the actives at temperatures in the range from about 5° C. to about 45° C. and at a pH that is in the range from about 3.0 to about 3.5, all over a time period up to at least about 4 days or more.

17 Claims, No Drawings

(56) References Cited

OTHER PUBLICATIONS

Mintel, Anonymous, "Invisible Defense Universal Protection Spray" XP055881269, No. 7981435, www.gnpd.com.
Mintel, Anonymous, "Ferulic Acid + Vitamins C and E Serum" XP055881272, No. 6433369, www.gnpd.com.
Mintel, Anonymous, "4D Defining Hydrator" XP055881273, No. 8511349, www.gnpd.com.
Mintel, "AHC Natural Perfection Pro Shield—Sun Perfector SPF 50+ PA++++", Record ID 7615847, May 2020, wwww.gnpd.com.
Mintel, "Auriga—Cernor Kit", Record ID 1630518, Sep. 2011, www.gnpd.com.
Mintel, "Drunk Elephant—Time to Wake Up a Morning Tonic for Skin", Record ID 7631131, May 2020, www.gnpd.com.
Mintel, "Drunk Elephant—Bare With Us the Love Kit", Record ID 7640457, May 2020, www.gnpd.com.
Mintel, "Drunk Elephant—Bare With Us the Love Kit", Record ID 77612403, May 2020, www.gnpd.com.
Mintel, "Drunk Elephant—Time to Wake Up a Morning Tonic for Skin", Record ID 7576779, Apr. 2020, www.gnpd.com.
Mintel, "Paula's Choice Boost—C15 Super Booster", Record ID 7201459, Jan. 2020, www.gnpd.com.
Mintel, "Pixi Skintreats Vitamin-C Chrsitmas 2019—Best of Vitamin-C Set", Record ID 7149163, Jan. 2020, www.gnpd.com.
Mintel, "Drunk Elephant—Rise + Glow Set", Record ID 7106385, Dec. 2019, www.gnpd.com.
Mintel, "Eighth Day—Dark Spot Rx", Record ID 6991279, Oct. 2019, www.gnpd.com.
Mintel, "Pixi Skintreats Vitamin C—Best of Vitamin C Set", Record ID 6529415 and 6449611, Apr. and May 2019, www.gnpd.com.
Mintel, "Eighth Day—Signature Collection", Record ID 6070639, Oct. 2018, www.gnpd.com.
Mintel, "Drunk Elephant—C-Firma Day Serum", Record ID 6038563, Oct. 2018, www.gnpd.com.
Mintel, "Eighth Day—Dark Spot Rx", Record ID 5955229, Oct. 2018, www.gnpd.com.
Mintel, "Korres—Rise & Shine Compete Shine Set", Record ID 5926015, Aug. 2018, www.gnpd.com.
Mintel, "Paula's Choice Boost—C15 Super Booster", Record ID 5821163 and 5821167, Jul. 2018, www.gnpd.com.
Mintel, "Paula's Choice Boost—C15 Super Booster", Record ID 5635233, Apr. 2018, www.gnpd.com.
Mintel, "Drunk Elephant—DayGLow Travel Sized Skin Care Set", Record ID 4533765, www.gnpd.com.

* cited by examiner

HYDROGLYCOLIC COSMETIC COMPOSITION WITH A HIGH ACTIVE CONTENT

FIELD

This invention relates to a water based composition for keratinous tissue, particularly skin, that includes one or more glycols and relatively high amounts of actives that benefit keratinous tissue.

BACKGROUND

UV exposure and environmental pollution can accelerate skin aging by producing free radicals in skin. Antioxidants, including Vitamin C, and other actives protect cells from the damage of oxidative stress by scavenging free radicals and inhibiting oxidation reactions. The topical application of antioxidants and other skin actives is broadly employed in skin care products to prevent skin aging. There are challenges with providing compositions that include suitably high amounts of actives, including antioxidants, in a system that can stably maintain solubility of the actives over time and at ambient temperatures. Some commercial compositions that are formulated with high amounts of actives suffer from short shelf lives or their effectiveness is diminished due to instability and ultimate precipitation of actives. Thus, many commercial compositions include amounts of actives that may be insufficient for addressing the risks faced by a consumer. There remains a need for systems for formulating protective compositions and protective compositions that offer meaningful levels of protective actives in a formulation that is chemically stable (wherein actives do not precipitate, decompose or react as evidenced by one or more of crystal formation, measured loss of solubility, and/or the composition becomes cloudy). In addition, there is a need for compositions that retain phase stability (do not form additional separate phases).

SUMMARY

The disclosure relates to a hydroglycolic cosmetic composition with a high active content that demonstrates stable solubilization of the actives (i.e., is chemically stable) at temperatures in the range from about 5° C. to about 45° C. and at a pH that is in the range from about 3.0 to about 3.5, all over a time period up to at least about 4 days or more, or up to at least about 8 days, or up to at least about 10 days, or for a period of more than 4 days, or for a period of more than 8 days, or for a period of more than 10 days.

In some embodiments, the disclosure provides a hydroglycolic cosmetic composition comprising:
(a) at least one or a combination of skin actives comprising at least one or a combination of ascorbic acid, a cinnamic acid derivative, and Vitamin E; and
(b) a glycol or combination of glycols selected from the group consisting of: dipropylene glycol, pentylene glycol, hexylene glycol, a combination of dipropylene glycol and pentylene glycol, and a combination of dipropylene glycol and hexylene glycol.

In various embodiments, the composition demonstrates stability of solubility of the actives at temperatures in the range from about 5° C. to about 45° C. and at a pH that is in the range from about 3.0 to about 3.5.

In various embodiments, the total amount of skin care actives present in the composition is in a range from about 16% to about 30%, based on the weight of the composition.

In various embodiments, the glycol or combination of glycols is selected from the group consisting of: (i) dipropylene glycol present in the composition in a range from at least about 10% to less than about 30%; (ii) pentylene glycol present in the composition in a range from at least about 8% to less than about 30%; (iii) hexylene glycol present in the composition in a range from at least about 8% to less than about 30%; (iv) a combination of pentylene glycol and dipropylene glycol present in a ratio that is in a range from about 1:6 to about 3:1 pentylene glycol to dipropylene glycol; and (v) a combination of hexylene glycol and dipropylene glycol present in a ratio that is in a range from about 1:6 to about 3:1 hexylene glycol to dipropylene glycol, wherein the total amount of a combination of glycols present in the composition is in a range from at least about 10% to less than about 30%, all amounts and ratios based on the weight of the composition.

In various embodiments, the composition comprises water in a range from about 40% up to about 75%, based on the weight of the composition.

In various embodiments, the at least one or a combination of skin actives comprises ascorbic acid present in the composition in a range from about 1% to about 30%, the ascorbic acid present in a ratio of water to ascorbic acid in a range from about 3:1 to about 10:1, based on the weight of the composition.

In various embodiments, the at least one or a combination of skin actives comprises each of ascorbic acid, a cinnamic acid derivative, and Vitamin E, the composition further comprising at least one surfactant. The surfactant may be any one of a nonionic, cationic, anionic or zwitterionic surfactant.

In various embodiments, the at least one surfactant is selected from the group consisting of polyoxyethylene sorbitan monolaureate, laureth-23, polyoxyethylated octyl phenol, 3-((3-cholamidopropyl) dimethylammonio)-1 propane sulfonate, sodium dilauramidoglutamide lysine, cholate, deoxycholate, sodium dodecylsulfate, TWEEN-80, and combinations thereof, all excluding esters, In various embodiments, the at least one surfactant is present in the composition in a range from about 1% to about 5%, based on the weight of the composition.

In various embodiments, the at least one surfactant is present in the composition in a ratio of surfactant to Vitamin E in a range from about 2:1 to greater than 3:1, based on the weight of the composition.

In various embodiments, the cinnamic acid derivative is ferulic acid and wherein the Vitamin E is a tocopherol.

In various embodiments, the at least one or a combination of skin actives further comprises a skin active selected from the group consisting of phytic acid, carnosine, chlorogenic acid, hyaluronic acid, panthenol, a sun filter, at least one hydroxy acid, and combinations thereof.

In various embodiments, the at least one or a combination of skin actives comprises a skin active selected from the group consisting of alpha, beta or polyhydroxy acids selected from the group consisting of lactic acid, glycolic acid, salicylic acid, malic acid, tartaric acid, citric acid, mandelic acid, lactobionic acid, gluconolactone, galactose, and combinations thereof.

In various embodiments, the composition comprises at least one oil and at least one surfactant, wherein the at least one surfactant is present in the composition in a ratio of surfactant to oil in a range from about 2:1 to greater than 3:1, based on the weight of the composition.

In various embodiments, the composition further includes one or more additives selected from fragrances, preservatives, anti-microbials, coloring materials, essential oils, citric acid, sodium citrate, sodium chloride, pH-adjusting agents, chelating agents, and combinations thereof, and is free or essentially free of powders and solid particles, including but not limited to, titanium dioxide, zinc oxide, tin oxide, iron oxides, mica, silica, ferric ferrocyanide, alumina, silicates, synthetic fluorphlogopite, polyethylene, polypropylene, poly methyl methacrylate, talc, perlites, hectorites, bentonite, kaolin, pumice, boron nitride, and combinations thereof, and wherein the composition excludes propylene glycol and butylene glycol.

In some embodiments, the disclosure provides a hydroglycolic cosmetic composition comprising:
(a) at least one or a combination of skin actives comprising at least each of:
  i. ascorbic acid present in the composition in a range from about 1% to about 30% and in a ratio of water to ascorbic acid in a range from about 3:1 to about 10:1, based on the weight of the composition,
  ii. a cinnamic acid derivative, and
  iii. Vitamin E;
(b) at least one surfactant; and
(c) a glycol or combination of glycols selected from the group consisting of: (i) dipropylene glycol present in the composition in a range from at least about 10% to less than about 30%; (ii) pentylene glycol present in the composition in a range from at least about 8% to less than about 30%; (iii) hexylene glycol present in the composition in a range from at least about 8% to less than about 30%; (iv) a combination of pentylene glycol and dipropylene glycol present in a ratio that is in a range from about 1:6 to about 3:1 pentylene glycol to dipropylene glycol; and (v) a combination of hexylene glycol and dipropylene glycol present in a ratio that is in a range from about 1:6 to about 3:1 hexylene glycol to dipropylene glycol, wherein the total amount of a combination of glycols present in the composition is in a range from at least about 10% to less than about 30%, all amounts and ratios based on the weight of the composition,
wherein the composition demonstrates stability of solubility of the actives at temperatures in the range from about 5° C. to about 45° C. and at a pH that is in the range from about 3 to about 3.5.

In various embodiments, the cinnamic acid derivatives comprises ferulic acid wherein the Vitamin E is a tocopherol, and wherein the total amount of skin care actives present in the composition is in a range from about 16% to about 30%, based on the weight of the composition.

In various embodiments, the at least one or a combination of skin actives further comprises a skin active selected from the group consisting of phytic acid, carnosine, chlorogenic acid, hyaluronic acid, panthenol, a sun filter, at least one hydroxy acid, and combinations thereof, and wherein the composition excludes propylene glycol and butylene glycol.

In some embodiments, the disclosure provides a method for providing a hydroglycolic cosmetic hydroglycolic cosmetic composition, the method comprising:
(a) providing at least one or a combination of skin actives comprising at least one or a combination of ascorbic acid, a cinnamic acid derivative, and Vitamin E, and optionally one or a more skin active selected from the group consisting of phytic acid, carnosine, chlorogenic acid, hyaluronic acid, panthenol, a sun filter, at least one hydroxy acid, and combinations thereof;
(b) providing at least one or a combination of glycols selected from the group consisting of: (i) dipropylene glycol present in the composition in a range from at least about 10% to less than about 30%; (ii) pentylene glycol present in the composition in a range from at least about 8% to less than about 30%; (iii) hexylene glycol present in the composition in a range from at least about 8% to less than about 30%; (iv) a combination of pentylene glycol and dipropylene glycol present in a ratio that is in a range from about 1:6 to about 3:1 pentylene glycol to dipropylene glycol; and (v) a combination of hexylene glycol and dipropylene glycol present in a ratio that is in a range from about 1:6 to about 3:1 hexylene glycol to dipropylene glycol, wherein the total amount of a combination of glycols present in the composition is in a range from at least about 10% to less than about 30%, all amounts and ratios based on the weight of the composition; and
(c) optionally providing one or more additives selected from fragrances, preservatives, anti-microbials, coloring materials, essential oils, citric acid, sodium citrate, sodium chloride, pH-adjusting agents, chelating agents, and combinations thereof, and is free or essentially free of powders and solid particles; and
(d) combining the at least one or a combination of skin actives and the at least one or a combination of glycols and any optional additives to provide a composition wherein each of the skin actives in the at least one or combination of skin actives is solubilized in the composition.

In some embodiments, the at least one or a combination of skin actives comprises each of ascorbic acid, a cinnamic acid derivative, and Vitamin E, the composition further comprising at least one surfactant.

In some embodiments, ascorbic acid is present in the composition in a range from about 1% to about 30% and in a ratio of water to ascorbic acid in a range from about 3:1 to about 10:1, the cinnamic acid derivative is ferulic acid, the Vitamin E is a tocopherol, wherein the at least one surfactant is present in the composition in ratio of surfactant to Vitamin E in a range from about 2:1 to greater than 3:1, and wherein the composition excludes propylene glycol and butylene glycol. all amounts and ratios based on the weight of the composition.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

"Cosmetically acceptable" means a carrier that is compatible with any keratinous substrate.

"Keratinous substrate" and "keratinous tissue" each includes but is not limited to skin, hair, and nails.

The composition according to the disclosure includes at least one or a combination of skin actives comprising at least one or a combination of ascorbic acid, a cinnamic acid derivative, and Vitamin E and at least one or a combination of glycols selected from the group consisting of dipropylene glycol, pentylene glycol, hexylene glycol, ethoxydiglycol, and combinations of dipropylene glycol with one of pentylene glycol and hexylene glycol. The composition demonstrates stability of solubility of the actives at temperatures in the range from about 5° C. to about 45° C. and at a pH that is in the range from about 3.0 to about 3.5.

The composition according to the disclosure is a single phase solution that comprises one or more solutes dissolved in one or more solvents to form a substantially homogeneous liquid that appears to be substantially clear to the naked eye. In one such embodiment, the composition is a single phase water solution.

The inventors have shown the surprising and unexpected relationship between specific glycols and combinations of specific glycols present in specific ratios yield significantly increased solubility of high amounts of actives.

Skin Actives

In accordance with the disclosure, embodiments of the composition include at least one or a combination of skin actives comprising at least one or a combination of ascorbic acid (Vitamin C), a cinnamic acid derivative, and Vitamin E. In some embodiments, the composition comprises each of ascorbic acid, a cinnamic acid derivative, and Vitamin E. In some specific embodiments, the composition comprises each of ascorbic acid, a cinnamic acid derivative comprising ferulic acid, and Vitamin E comprising tocopherol. In some further specific embodiments, the composition also comprises phytic acid, carnosine, chlorogenic acid, hyaluronic acid, panthenol, a sun filter, at least one hydroxy acid, or combinations thereof. In some further specific embodiments, the composition comprises each of ascorbic acid, ferulic acid, tocopherol, hyaluronic acid, panthenol and one of phytic acid and carnosine.

In some embodiments, the at least one or a combination of skin actives comprises ascorbic acid, also known as Vitamin C. The pH of the composition in the range from about 3.0 to about 4.0, and more particularly about 3.5, ensures that greater than about 82% of the ascorbic acid remains in a protonated, uncharged form as disclosed in U.S. Pat. No. 5,140,043, Aug. 18, 1992, the entire disclosure of which is incorporated by reference herein. Ascorbic acid may be provided by the addition of any reducing analog of ascorbic acid, such as D-isoascorbic acid or by the addition of other small reducing compounds such as, but not limited to, glutathione, L-cysteamine, and the like. Such forms would be expected to provide an equivalent composition to that claimed and are within the scope of the invention.

In some embodiments, the at least one or a combination of skin actives comprises a cinnamic acid derivative. A cinnamic acid or derivative thereof may be selected from the group consisting of ferulic acid, p-coumaric acid, caffeic acid, sinapinic acid, chlorogenic acids, caftaric acid, chicoric acid, coutaric acid, rosmarinic acid, derivatives thereof, and combinations thereof. Equivalent derivatives thereof include those cinnamic acid derivatives having substitutions on the hydroxyl groups of the aromatic ring such as short chain aliphatic groups (one to six carbon atoms) or long chain aliphatic groups (seven to twenty-four carbon atoms) to form an ether, or such aliphatic groups substituted with alkyl, alkoxy, hydroxyl, amino, or amido, for example, to form a substituted ether. Equivalent derivatives thereof further include those cinnamic acid derivatives having modifications of the methoxy group(s) of the aromatic ring to short chain aliphatic groups (two to six carbon atoms) or to long chain aliphatic groups (seven to twenty-four carbon atoms) to form a longer chain ether, or such aliphatic groups substituted with alkyl, alkoxy, hydroxyl, amino, or amido, for example, to form a substituted long chain ether. The 3-carboxy group of a cinnamic acid derivative may also be converted to esters or amides having aliphatic groups of up to 24 carbons or an aromatic group, for example. Cis and trans isomers of the cinnamic acid derivatives are included herein since the cis isomer is readily converted to the trans isomer. Salts of the cinnamic acid derivatives are included herein. In one embodiment, the cinnamic acid derivative is a triethanolamine salt. Caffeic acid, also known as 3-(3,4-dihydroxyphenyl)-2-propenoic acid, is found in many fruits, vegetables, seasonings and beverages consumed by humans. Caffeic acid is present in such goods in conjugated forms such as chlorogenic acid. Para-coumaric acid, also known as 3-(4-hydroxyphenyl)-2-propenoic acid or p-hydroxycinnamic acid, is found in various plants, including lignin forming plants. Trans-ferulic acid, also known as 3-(4-hydroxy-3-methoxyp-henyl)-2-propenoic acid or 4-hydroxy-3-methoxycinnamic acid, is also widely distributed in small amounts in plants. Sinapinic acid, also known as 3,5-dimethoxy4-hydroxycinnamic acid, is from black mustard seeds. Caffeic acid, para-coumaric acid, trans-ferulic acid and sinapinic acid are commercially available from Sigma-Aldrich.

In some embodiments, the at least one or a combination of skin actives comprises Vitamin E or a derivative thereof. Vitamin E may be selected from the group consisting of alpha-tocopherol, beta-tocopherol, delta-tocopherol, gamma-tocopherol, and alpha-tocotrienol, beta-tocotrienol, delta-tocotrienol, gamma-tocotrienol, and derivatives thereof. Salts or derivatives of tocopherols include pharmaceutically acceptable compounds such as acetate, sulfate, succinate, nicotinate, palmitate, allophanate, phosphate, quinone, or halogenated derivatives, esters, or stereoisomers, for example. The invention encompasses the use of Vitamin E derivatives in which substitutions, additions, and other alterations have been made in the 6-chromanol ring and/or side chain, with the proviso that the derivatives maintain the antioxidant activity of Vitamin E. Additional tocopherols can be constructed by conjugation to the ring structure or side chain of various other moieties, such as those containing oxygen, nitrogen, sulfur and/or phosphorus. Tocopherol derivatives can also be made by modifying the length of the side chain from that found in tocopherols such as alpha-, beta-, delta- and gamma-tocopherol. Tocopherols can also vary in stereochemistry and saturation of bonds in the ring structure and side chain. Additional tocopherol derivatives, including prodrugs, can be made by conjugation of sugars or other moieties to the side chain or ring structure. Tocopherols include without limitation stereoisomers (e.g., + and − stereoisomers of alpha-tocopherol; (+/−) indicates a racemic mixture) or mixtures of structurally distinct tocopherols (e.g., alpha-plus gamma-tocopherol). Tocopherols may be obtained from Roche, Nutley, N.J., for example.

In some embodiments, additional actives can also include at least one hydroxy acid selected from alpha, beta or polyhydroxy acids. Thus, in various embodiments, a hydroxy acid may be selected from the group consisting of lactic acid, glycolic acid, salicylic acid, malic acid, tartaric acid, citric acid, mandelic acid, lactobionic acid, gluconolactone, galactose, and combinations thereof.

In some embodiments, additional actives can also include antioxidants selected from the group consisting of mangiferin, baicalin, resveratrol, tannic acid, polyphenols, amino acids and derivatives thereof, imidazoles, carnosine derivatives, carotenoids, carotenes (such as α-carotene, β-carotene, and lycopene), vitamin A, co-enzyme Q10, bioflavonoids, glutathione, plant extracts (such as rosemary extract, olive leaf extracts), green tea extracts, and combinations thereof.

In various embodiments, each skin active in the at least one or a combination of skin actives comprising at least one or a combination of ascorbic acid, a cinnamic acid derivative, and Vitamin E, the combination present in the composition at a concentration, from about 15% to about 30%, and in some embodiments, from about 16% to about 30%, and in some embodiments, from about 16% to about 25%, and in some embodiments, from about 16.5% to about 24%, or any suitable combination, sub-combination, range, or sub-range thereof by weight, based on the weight of the composition.

Generally, each of the skin actives is present in the composition in an amount from about 0.1% to about 30%, and in some embodiments, from about 0.5% to about 30%, and in some embodiments, from about 0.5% to about 15%, and in some embodiments, from about 0.1% to about 1%, and in some embodiments, from about 1% to about 2%, or any suitable combination, sub-combination, range, or sub-range thereof by weight, based on the weight of the composition.

Ascorbic acid and its derivatives may be present in the composition in an amount from about 1% to about 30%, and in some embodiments, from about 5% to about 25%, and in some embodiments, from about 10% to about 20%, and in some embodiments, from about 10% to about 15%, or any suitable combination, sub-combination, range, or sub-range thereof by weight, based on the weight of the composition.

Cinnamic acid derivatives, including, but not limited to ferulic acid, and triethanolamine salts may be present in the compositions in an amount from about 0.1% to about 5%, and in some embodiments, from about 0.1% to about 3%, and in some embodiments, from about 0.5% to about 1.0%, or any suitable combination, sub-combination, range, or sub-range thereof by weight, based on the weight of the composition.

Vitamin E and its derivatives, including, but not limited to tocopherol, may be present in the compositions in an amount from about 0.5% to about 2%, and in some embodiments, from about 0.5% to about 1%, and in some embodiments, from about 1% to about 2.0%, or any suitable combination, sub-combination, range, or sub-range thereof by weight, based on the weight of the composition.

Phytic acid, carnosine, chlorogenic acid, hyaluronic acid, panthenol, may be present in the compositions in an amount from about 0.1% to about 5%, and in some embodiments, from about 0.1% to about 3%, and in some embodiments, from about 0.5% to about 1.0%, or any suitable combination, sub-combination, range, or sub-range thereof by weight, based on the weight of the composition.

Phytic acid may be present in the compositions in an amount from about 0.5% to about 5%, and in some embodiments, from about 1% to about 4%, and in some embodiments, from about 1% to about 2%, or any suitable combination, sub-combination, range, or sub-range thereof by weight, based on the weight of the composition. As exemplified in the instant disclosure, the phytic acid raw material is provided at a dilution of 50% such that the exemplified weight percents in the compositions are multiplied by 0.5 to obtain the final weight percent of phytic acid.

Carnosine may be present in the compositions in an amount from about 0.10% to about 1%, and in some embodiments, from about 0.20% to about 0.5%, and in some embodiments, from about 0.20% to about 0.25%, or any suitable combination, sub-combination, range, or sub-range thereof by weight, based on the weight of the composition.

Chlorogenic acid may be present in the compositions in an amount from about 0.5% to about 1.5%, and in some embodiments, from about 1% to about 1.5%, and in some embodiments, from about 1.1% to about 1.2%, or any suitable combination, sub-combination, range, or sub-range thereof by weight, based on the weight of the composition.

Hyaluronic acid may be present in the compositions in an amount from about 0.01% to about 1%, and in some embodiments, from about 0.01% to about 0.1%, and in some embodiments, from about 0.05% to about 0.07%, or any suitable combination, sub-combination, range, or sub-range thereof by weight, based on the weight of the composition.

Panthenol may be present in the compositions in an amount from about 0.1% to about 1%, and in some embodiments, from about 0.1% to about 0.5%, and in some embodiments, from about 0.2% to about 0.4%, and in some embodiments, from about 0.2% to about 0.25%, or any suitable combination, sub-combination, range, or sub-range thereof by weight, based on the weight of the composition.

A hydroxy acid may be present in the compositions in an amount from about 0.25% to about 10%, and in some embodiments, from about 0.5% to about 8%, and in some embodiments, from about 1% to about 5%, and in some embodiments, from about 0.25% to about 0.5%, or any suitable combination, sub-combination, range, or sub-range thereof by weight, based on the weight of the composition.

In accordance with some embodiments, the composition comprises more than one skin care active, the combination thereof present in the composition at a total concentration, from about 15% to about 30%. In some embodiments, the total amount of skin care actives present in the composition is in a range from about 16% to about 30%, based on the weight of the composition.

In some particular embodiments, the composition includes a combination present in the composition in a range from about 16% to about 30%, based on the weight of the composition, selected from: (i) ascorbic acid, ferulic acid, tocopherol, panthenol, and hyaluronic acid; (ii) ascorbic acid, ferulic acid, tocopherol, panthenol, hyaluronic acid, and phytic acid; (iii) ascorbic acid, ferulic acid, tocopherol, panthenol, hyaluronic acid, and phytic acid; (iv) ascorbic acid, ferulic acid, tocopherol, panthenol, hyaluronic acid, and phytic acid; (v) ascorbic acid, ferulic acid, tocopherol, panthenol, hyaluronic acid, and chlorogenic acid; (vi) ascorbic acid, ferulic acid, tocopherol, panthenol, hyaluronic acid, chlorogenic acid, and phytic acid; (vii) ascorbic acid, ferulic acid, tocopherol, panthenol, hyaluronic acid, chlorogenic acid, phytic acid, and sun filter (UV agent); and (viii) ascorbic acid, ferulic acid, tocopherol, panthenol, hyaluronic acid, chlorogenic acid, phytic acid, and carnosine.

Thus, in various embodiments, each of the skin actives is present in a composition according to the disclosure and each of the individual components in the ranges provided herein above, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28 to about 30 percent by weight, including increments and ranges there between.

Glycols

In accordance with the disclosure, embodiments of the composition include a glycol or combination of glycols selected from the group consisting of: dipropylene glycol, pentylene glycol, hexylene glycol, a combination of dipropylene glycol and pentylene glycol, and a combination of dipropylene glycol and hexylene glycol. In accordance with various embodiments, each one of the glycols may be present in the composition alone or with at least one other glycol, each glycol present in an amount that is in a range from about 0.1% to about 30% by weight, based on the weight of the composition. In some embodiments, the total amount of glycol is less than about 30%, for example, the total is about 29.5%, or about 29%. As provided herein, some glycols, when present alone in the composition, are present in an amount that is at least about 8%, or at least about 8.5%, or at least about 9%, or at least about 9.5%, or at least about 10%, or at least about 10.5%.

Dipropylene Glycol

In various embodiments, the glycol or combination of glycols may comprise dipropylene glycol present in the composition in a range from at least about 10% to less than about 30%. Dipropylene glycol may be present in the composition in an amount from at least about 10.5% to less than about 30%, and in some embodiments, from about 11% to about 25%, and in some embodiments, from about 12% to about 20%, and in some embodiments, from about 13% to about 15%, or any suitable combination, sub-combination, range, or sub-range thereof by weight, based on the weight of the composition.

Pentylene Glycol

In various embodiments, the glycol or combination of glycols may comprise pentylene glycol present in the composition in a range from at least about 8% to less than about 30%. Pentylene glycol may be present in the composition in an amount from at least about 8.5% to less than about 30%, and in some embodiments, from about 9% to about 25%, and in some embodiments, from about 10% to about 20%, and in some embodiments, from about 13% to about 15%, or any suitable combination, sub-combination, range, or sub-range thereof by weight, based on the weight of the composition.

Hexylene Glycol

In various embodiments, the glycol or combination of glycols may comprise hexylene glycol present in the composition in a range from at least about 8% to less than about 30%. Hexylene glycol may be present in the composition in an amount from at least about 8.5% to less than about 30%, and in some embodiments, from about 9% to about 25%, and in some embodiments, from about 10% to about 20%, and in some embodiments, from about 13% to about 15%, or any suitable combination, sub-combination, range, or sub-range thereof by weight, based on the weight of the composition.

Pentylene Glycol and Dipropylene Glycol

In various embodiments, the glycol or combination of glycols may comprise a combination of pentylene glycol and dipropylene glycol.

When provided in combination, each of pentylene glycol and dipropylene glycol may be present in a range from about 0.1% to about less than 30%, wherein the total amount of the combination of glycols present in the composition is in a range from at least about 10% to less than about 30%, and in some embodiments from at least about 10.5% to less than about 30%, all amounts and ratios based on the weight of the composition.

According to such embodiments, pentylene glycol and dipropylene glycol may be present in a ratio that is in a range from about 1:100 to about 100:1 pentylene glycol to dipropylene glycol, wherein the combination is present up to less than about 30% by weight of the composition. According to some embodiments, pentylene glycol and dipropylene glycol may be present in a ratio that is in a range from about 1:6 to about 3:1 pentylene glycol to dipropylene glycol. In some embodiments, the ratio of pentylene glycol to dipropylene glycol is 1:6, and in some embodiments it is 1:3, and in some embodiments, it is 1:1, and in some embodiments it is 1:3.

In some embodiments, pentylene glycol may be present in the combination within the composition in an amount from at least about 1.5% and up to less than about 13%, and in some embodiments, from about 6% to about 8.5%, and in some embodiments, from about 3% to about 5.5%, and in some embodiments, from about 1.5% to about 2.5%, or any suitable combination, sub-combination, range, or sub-range thereof by weight, based on the weight of the composition.

In some embodiments, dipropylene glycol may be present in the combination within the composition in an amount from at least about 2.5% and up to less than about 25%, and in some embodiments, from about 4% to about 20%, and in some embodiments, from about 5% to about 10%, and in some embodiments, from about 5.5% to about 8.5%, or any suitable combination, sub-combination, range, or sub-range thereof by weight, based on the weight of the composition.

Hexylene Glycol and Dipropylene Glycol

In various embodiments, the glycol or combination of glycols may comprise a combination of hexylene glycol and dipropylene glycol. Hexylene glycol is also referred to as "2-methyl-2,4-pentanediol" or simply "methyl-2,4-pentanediol."

When provided in combination, each of hexylene glycol and dipropylene glycol may be present in a range from about 0.1% to about less than 30%, wherein the total amount of the combination of glycols present in the composition is in a range from at least about 10% to less than about 30%, and in some embodiments from at least about 10.5% to less than about 30%, all amounts and ratios based on the weight of the composition.

According to such embodiments, hexylene glycol and dipropylene glycol may be present in a ratio that is in a range from about 1:100 to about 100:1 hexylene glycol to dipropylene glycol, wherein the combination is present up to less than about 30% by weight of the composition. According to some embodiments, hexylene glycol and dipropylene glycol may be present in a ratio that is in a range from about 1:6 to about 3:1 hexylene glycol to dipropylene glycol. In some embodiments, the ratio of hexylene glycol to dipropylene glycol is 1:6, and in some embodiments it is 1:3, and in some embodiments, it is 1:1, and in some embodiments it is 1:3.

In some embodiments, hexylene glycol may be present in the combination within the composition in an amount from at least about 1.5% and up to less than about 13%, and in some embodiments, from about 6% to about 8.5%, and in some embodiments, from about 3% to about 5.5%, and in some embodiments, from about 1.5% to about 2.5%, or any suitable combination, sub-combination, range, or sub-range thereof by weight, based on the weight of the composition.

In some embodiments, dipropylene glycol may be present in the combination within the composition in an amount from at least about 2.5% and up to less than about 25%, and in some embodiments, from about 4% to about 20%, and in some embodiments, from about 5% to about 10%, and in some embodiments, from about 5.5% to about 8.5%, or any suitable combination, sub-combination, range, or sub-range thereof by weight, based on the weight of the composition.

Thus, in various embodiments, each of the glycols is present in a composition according to the disclosure, each alone and/or in combinations as described in the paragraphs set forth herein above from about 0.1, 0.2, 0.3, 0.4, 0.5, 0.6, 0.7, 0.8, 0.9, 1.0, 1.5, 2, 3, 4, 5, 6, 7, 8, 9, 10, 11, 12, 13, 14, 15, 16, 17, 18, 19, 20, 21, 22, 23, 24, 25, 26, 27, 28, 29 to less than about 30 percent, by weight, including increments and ranges therein and there between.

Surfactant

In accordance with the disclosure, various non-limiting embodiments of the composition may optionally include at least one surfactant. And in accordance with the disclosure, various non-limiting embodiments of the composition that include an oil, for example, but not limited to, a Vitamin E component, such as tocopherol, may optionally include at least one surfactant. In some embodiments, the composition comprises no oil. In some embodiments, the composition comprises no surfactant. In some embodiments, the composition comprises at least one oil, for example, tocopherol, with at least one surfactant. In some embodiments, the composition comprises at least one oil with more than one surfactant. In some embodiments, the composition comprises at least one oil without any surfactants, wherein the total amount of oil present does not inhibit forming the composition as a clear, single phase solution.

The at least one surfactant may be an nonionic, cationic, anionic, or a zwitterionic surfactant. The at least one surfactant may be selected from the group consisting of polyoxyethylene sorbitan monolaureate, laureth-23, polyoxyethylated octyl phenol, 3-((3-cholamidopropyl)dimethylammonio)-1 propane sulfonate, sodium dilauramidoglutamide lysine, cholate, deoxycholate, sodium dodecylsulfate, TWEEN-80, and combinations thereof. The at least one surfactant may exclude esters. The at least one surfactant may be present in the composition in a range from about 1% to about 5%, based on the weight of the composition.

In some particular embodiments the at least one surfactant comprises one or a combination of polyoxyethylene sorbitan monolaureate and laureth-23.

In various embodiments, the at least one surfactant may be present from about 1% to about 5% by weight of the composition, and in some embodiments, from about 1% to about 2%, and in some embodiments, from about 3% to about 6%, and in some embodiments, from about 3% to about 4.5%, or any suitable combination, sub-combination, range, or sub-range thereof by weight, based on the weight of the composition. In some embodiments, laureth-23 may be present from about 1% to about 5% by weight of the composition, and in some embodiments, from about 3% to about 4.5%, or any suitable combination, sub-combination, range, or sub-range thereof by weight, based on the weight of the composition. In some embodiments, polyoxyethylene sorbitan monolaureate may be present from about 1% to about 5% by weight of the composition, and in some embodiments, from about 1% to about 2%, or any suitable combination, sub-combination, range, or sub-range thereof by weight, based on the weight of the composition. In some embodiments, the composition comprises more than one surfactant. One of ordinary skill in the art, however, will appreciate that other ranges are within the scope of the invention.

Thus, in various embodiments, when present, each of the at least one surfactant may be present in a composition according to the disclosure from about 1, 2, 3, 4, to about 5 percent, by weight, including increments and ranges therein and there between.

Water

In accordance with the various embodiments, water is present in the compositions in a range from about 40% to about 75%, and in some embodiments, from about 45% to about 70%, and in some embodiments, from about 50% to about 65%, and in some embodiments, from about 55% to about 60%, and in some embodiments, about 68% or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, to about 75 percent, by weight, including increments and ranges therein and there between. One of ordinary skill in the art, however, will appreciate that other ranges are within the scope of the invention.

The water used may be chosen from, for example, sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally between 3.0 and 4.0, and in some embodiments, is one of between 3 and 3.5. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid. It will be understood by a skilled artisan that pH is a measurement of the hydrogen ion concentration in water which is determined by measuring the electrode potential using electrodes attached to a pH meter. It will be further understood that, due to the intrinsic variability in pH measurements, a skilled artisan would expect at least a 10% variability in pH measurements of compositions such as disclosed herein when measured in a typical laboratory by a typical skilled person using a typical pH meter Optional Additives The compositions may also comprise at least one additive used in the cosmetics field which does not affect the properties of the compositions according to the invention, such as fragrances, preservatives, anti-microbials, coloring materials, essential oils, citric acid, sodium citrate, sodium chloride, pH-adjusting agents, chelating, and combinations thereof. In some particular embodiments, the compositions may comprise at least one additive selected from: preservatives/anti-microbials, for example, phenoxyethanol, potassium sorbate, and caprylyl glycol; actives, for example, hydroxyacetophenone, and vitamins, and UV agents such as terephthalylidene dicamphor sulfonic acid; coloring materials; essential oils; citric acid, sodium citrate, sodium chloride; neutralizing, chelating or pH-adjusting agents (for example, triethylamine (TEA), trisodium ethylenediamine disuccinate, and sodium hydroxide), and combinations thereof.

Preservatives having antibacterial activity are optionally present in the compositions of the present invention. Any preservative commonly used in cosmetic formulations is an acceptable preservative for the compositions herein, such as phenoxyethanol, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorophenesin, or salicylic acid, for example. At more concentrated amounts of suitable solvents for optional additives, in particular, suitable solvents for antimicrobials and preservatives, members from the paraben family may be used as a preservative.

Although the optional additives are given as examples, it will be appreciated that other optional components compatible with cosmetic applications known in the art may be used that are suitable. It will be appreciated by a skilled artisan that any optional additives are present only to the extent and in amounts that do not materially adversely affect the basic and novel characteristic(s) of the claimed disclosure. Thus, in some embodiments that include optional additives, such optional additives will not materially adversely affect the solubility of the skin actives of the composition. And in some embodiments that include optional additives, such optional additives will not materially adversely affect the composition forming a single phase solution.

In some particular embodiments, the composition may include optional additives, for example one or more of phenoxyethanol, terephthalylidene dicamphor sulfonic acid, trisodium ethylenediamine disuccinate, sodium citrate, sodium chloride, hydroxyacetophenone sodium benzoate, potassium sorbate, citric acid, caprylyl glycol, trisodium ethylenediamine disuccinate, or combinations thereof. In some embodiments, phenoxyethanol is present as a preservative in the composition in a range from about 0.5% to about 2%, and in some embodiments in a range from about 1% to about 2%.

In accordance with the various embodiments, the amount of one or more actives and additives, alone or in combination, when present in the composition according to the disclosure can be present in a range from about 0.001% to about 20%, and in some embodiments, from about 0.05% to about 0.01%, and in some embodiments, from about 0.01% to about 0.1%, and in some embodiments, from about 0.15% to about 5%, and in some embodiments, from about 0.40% to about 4%, and in some embodiments, from about 0.5% to about 2.5%, and in some embodiments, from about 0.1% to about 0.5%, and in some embodiments, from about 1% to about 2%, or any suitable combination, sub-combination, range, or sub-range thereof by weight, based on the total weight of the composition. One of ordinary skill in the art, however, will appreciate that other ranges are within the scope of the invention.

Thus, any one or a combination of actives and additives may be present, each one or the combination present from about 0.001, 0.005, 0.01, 0.02, 0.03, 0.04, 0.05, 0.06, 0.07, 0.08, 0.09, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, including increments and ranges therein and there between.

Formulations

The composition of the present invention may be used for the production of cosmetic preparations, or dermatological preparations, more particularly topical treatment preparations, that may be formulated as single-phase solution compositions, cosmetic serums, or aerosols, for example. Topical application to a surface may be a surface such as the mucus membrane or the skin, for example.

Process of Making Stabilized Ascorbic Acid Composition without oil/tocopherol:

The disclosure provides a composition that is stable. As used herein, stable means and includes: Physical stability, wherein, over a predetermined time, the actives remain solubilized in solution and do not crystallize out, such phase stability evidenced by the absence of visually discernable crystal formation or by direct chemical measurement of solubilized active, or both; and Phase stability, wherein the composition remains as a single phase, clear solution, that does not separate into more than one layer, or become cloudy (which could be evidence of chemical breakdown of one or more actives), such physical stability evidenced by visual inspection. For purposes hereof, a composition that demonstrates physical stability and does not become cloudy, as evidenced by visual inspection, is presumed to be chemically stable, such that the actives remain soluble and do not decompose or chemically react to form non-active compounds in a manner that would diminish or eliminate their capability of acting according to their intended function at that time of application. As disclosed and exemplified herein, an inventive composition remains chemically stable (wherein actives do not precipitate, decompose or react as evidenced by one or more of crystal formation, measured loss of solubility, and/or the composition becomes cloudy), at temperatures in the range from about 5° C. to about 45° C. and at a pH that is in the range from about 3.0 to about 3.5, all over a time period up to at least about 4 days or more, or up to at least about 8 days, or up to at least about 10 days, or for a period of more than 4 days, or for a period of more than 8 days, or for a period of more than 10 days.

Compositions according to the disclosure are made using the following procedures: water, solvents, and actives other than ascorbic acid and sodium hyaluronate are stirred together until dissolved to a clear solution. Sodium hyaluronate is sprinkled on the surface of the solution without stirring and the mixture allowed to form a gel without stirring for about 3 hours. After the three hour period, the gel is stirred to obtain a uniform viscous solution. The solution is degassed under vacuum and saturated with an inert gas such as argon or nitrogen. This degassing and saturating procedure was carried out three times. Ascorbic acid is added with stirring, the solution is again degassed under vacuum and saturated with an inert gas, and then stirred for 30 to 45 minutes to yield a clear solution which is then degassed and saturated with an inert gas.

Process of Making Stabilized Ascorbic Acid Composition with oil/tocopherol: A further embodiment of the present invention is a product made by a process described herein. Compositions having increased a hydrophobic component such as tocopherol are made by mixing water, actives other than ascorbic acid, tocopherol and sodium hyaluronate until a clear solution is formed. Sodium hyaluronate is sprinkled on the surface of the solution and allowed to dissolve for about three hours to form a first solution. Separately, a mixture that includes solvents, surfactant, the optional additive preservative, phenoxyethanol, and the hydrophobic component is gently heated with stirring to 60° C. to form a second solution. This second solution is then added to the first solution with stirring until the combined solution is clear. Cooling of the second solution is not required. The combined solution is degassed under vacuum with an inert gas such as saturated argon or nitrogen. The degassing and saturating is carried out three times. Ascorbic acid is added with stirring. The final solution is degassed and saturated with the inert gas and stirred to form a clear solution.

Methods of Use of Stabilized Ascorbic Acid Compositions: The present disclosure also provides a method of treating a condition of a subject that results from radical damage comprising administering a composition of the present invention to the subject. Treating, as used herein, means prophylactic and/or therapeutic treatment of a subject. "Prophylactic" treatment is a treatment administered to a subject who does not have symptoms of radical-induced damage or has early signs of such damage or anticipates being exposed to situations having risk of radical-induced damage. "Therapeutic" treatment is a treatment administered to a subject who has signs of radical-induced damage. Such a condition may be photo-aging, or diseases or disorders of the skin such as skin cancer, skin irritation or inflammation, dermatitis, allergy, psoriasis, acne, eczema, rosacea, or radiation exposure, for example.

The examples below according to the invention are given by way of illustration and without a limiting nature. The names are the chemical name or the INCI name. The amounts are given therein as % by weight, unless otherwise mentioned.

EXAMPLES

Example 1

Inventive Compositions

Various representative embodiments of the inventive compositions and articles are exemplified herein.

TABLE 1

Inventive Compositions

| INCI US | INV 1 | INV 2 | INV 3 | INV 4 | INV 5 | INV 6 | INV 7 | INV 8 | INV 9 | INV 10 |
|---|---|---|---|---|---|---|---|---|---|---|
| PANTHENOL | 0.25 | 0.25 | 0.25 | 0.25 | 0.25 | 0.25 | 0.25 | 0.25 | 0.25 | 0.25 |
| HEXYLENE GLYCOL | 9.29 | 9.29 | 9.29 | 3.72 | 9.29 | 9.29 | 3.90 | 3.90 | 3.90 | 3.90 |
| ASCORBIC ACID | 15.0 | 15.0 | 15.0 | 20.0 | 15.0 | 15.0 | 20.0 | 20.0 | 20.0 | 20.0 |
| SODIUM HYDROXIDE | 0.0 | 0.0 | 0.0 | 0.0 | 0.0 | 0.0 | 0.0 | 0.0 | 0.0 | 0.0 |
| DIPROPYLENE GLYCOL | 15.71 | 15.71 | 15.71 | 6.28 | 15.71 | 15.71 | 6.60 | 6.60 | 6.60 | 6.60 |
| TOCOPHEROL | 1.0 | 1.0 | 1.0 | 1.50 | 1.0 | 1.0 | 1.50 | 1.50 | 1.50 | 1.50 |
| FERULIC ACID | 0.50 | 0.50 | | | 0.50 | 0.50 | 0.50 | 0.50 | 0.50 | 0.50 |
| WATER | qs | qs | qs | qs | qs | qs | qs | qs | qs | qs |
| PHENOXYETHANOL | 1.0 | 1.0 | 1.0 | 0.90 | 1.0 | 1.0 | 0.90 | 0.90 | 0.90 | 0.90 |
| LAURETH-23 | 3.0 | 3.0 | | | 3.0 | 3.0 | | 4.50 | | |
| SODIUM HYALURONATE | 0.07 | 0.07 | 0.07 | 0.07 | 0.07 | 0.07 | 0.07 | 0.07 | 0.07 | 0.07 |
| PHYTIC ACID | 2.0 | 2.0 | 4.0 | 4.0 | | 4.0 | 4.0 | | 8.0 | 6.0 |
| SODIUM DILAURAMIDOGLUTAMIDE LYSINE | | 2.0 | | | | 2.0 | | | | |
| TRIETHANOLAMINE | | | 0.50 | 0.50 | | | | | | |
| FERULIC ACID | | | 0.50 | 0.50 | | | | | | |
| LAURETH-23 | | | 3.0 | 4.50 | | | 4.50 | | 4.50 | 4.50 |
| CHLOROGENIC ACIDS | | | | | | | | | | |
| TEREPHTHALYLIDENE DICAMPHOR SULFONIC ACID | | | | | | | | | | |
| CARNOSINE | | | | | | | | | | |

TABLE 2

Inventive Compositions

| INCI US | INV 11 | INV 12 | INV 13 | INV 14 | INV 15 | INV 16 | INV 17 | INV 18 | INV 19 | INV 20 | INV 21 |
|---|---|---|---|---|---|---|---|---|---|---|---|
| PANTHENOL | 0.25 | 0.25 | 0.25 | 0.25 | 0.25 | 0.25 | 0.25 | 0.25 | 0.25 | 0.25 | 0.25 |
| HEXYLENE GLYCOL | 9.29 | 9.29 | 9.29 | 3.90 | 3.90 | 9.29 | 9.29 | 9.29 | 9.29 | 9.29 | 9.29 |
| ASCORBIC ACID | 15.0 | 15.0 | 15.0 | 20.0 | 18.0 | 15.0 | 15.0 | 15.0 | 15.0 | 15.0 | 15.0 |
| SODIUM HYDROXIDE | 0.0 | 0.0 | 0.0 | 0.0 | 0.0 | 0.0 | 0.0 | 0.0 | 0.0 | 0.0 | 0.0 |
| DIPROPYLENE GLYCOL | 15.7 | 15.7 | 15.7 | 6.60 | 6.60 | 15.7 | 15.7 | 15.7 | 15.7 | 15.7 | 15.7 |
| TOCOPHEROL | 1.0 | 1.0 | 1.0 | 1.50 | 1.50 | 1.0 | 1.0 | 1.0 | 1.0 | 1.0 | 1.0 |
| FERULIC ACID | 0.50 | 0.50 | | 0.50 | 0.50 | 0.50 | 0.50 | 0.50 | 0.50 | 0.50 | 0.50 |
| WATER | qs | qs | qs | qs | qs | qs | qs | qs | qs | qs | qs |
| PHENOXYETHANOL | 1.0 | 1.0 | 1.0 | 0.90 | 0.90 | 1.0 | 1.0 | 1.0 | 1.0 | 1.0 | 1.0 |
| LAURETH-23 | | | | | 4.50 | 3.0 | 3.0 | 3.0 | 3.0 | 3.0 | 3.0 |
| SODIUM HYALURONATE | 0.07 | 0.07 | 0.07 | 0.07 | 0.07 | 0.07 | 0.07 | 0.07 | 0.07 | 0.07 | 0.07 |
| PHYTIC ACID | | | 8.0 | | | 2.0 | 2.0 | 2.0 | 2.0 | 2.0 | 2.0 |
| SODIUM DILAURAMIDOGLUTAMIDE LYSINE | | 2.0 | 2.0 | | | | 1.0 | | 1.0 | | 1.0 |
| TRIETHANOLAMINE | 0.50 | 0.50 | 0.50 | | | | | | | | |
| FERULIC ACID | | | 0.50 | | | | | | | | |
| LAURETH-23 | 3.0 | 3.0 | 3.0 | 4.50 | | | | | | | |
| CHLOROGENIC ACIDS | 1.20 | 1.20 | 1.20 | 1.20 | | 1.20 | 1.20 | 1.20 | 1.20 | 1.20 | 1.20 |

TABLE 2-continued

Inventive Compositions

| INCI US | INV 11 | INV 12 | INV 13 | INV 14 | INV 15 | INV 16 | INV 17 | INV 18 | INV 19 | INV 20 | INV 21 |
|---|---|---|---|---|---|---|---|---|---|---|---|
| TEREPHTHALYLIDENE DICAMPHOR SULFONIC ACID | | | | | | | | 6.0 | 6.0 | | |
| CARNOSINE | | | | | | | | | | 0.25 | 0.25 |

Example 2

Demonstrating Stability of Compositions Containing High Amounts of Actives

A representative formula ("BASE FLA") containing 20% ascorbic acid, 0.5% ferulic acid, and 2% phytic acid along with 10.5% glycols was prepared. This formula also contains approximately 60% water; with a ratio of 3:1 water: ascorbic acid, the solubility limit of ascorbic acid in water is being approached. To test the solubility of actives in the formula, only the glycol was varied. The glycols tested were propylene, butylene, pentylene, hexylene, and dipropylene, as well as ethoxydiglycol. Each were tested alone at 10.5%, and in different combinations for a total content of 10.5%. After formulas were made, they were placed at 5° C. and in a freeze/thaw chamber to determine if any of the actives will crystallize out of solution. The results of the study are shown in Table 3.

TABLE 3

| Glycol in BASE FLA | | | | | |
|---|---|---|---|---|---|
| propylene | butylene | pentylene | hexylene | dipropylene | Result |
| 10.50% | | | | | Crystals 5° C. @ 4 days |
| | 10.50% | | | | Crystals 5° C. @ 4 days |
| | | 10.50% | | | PASS |
| | | 8.50% | | | PASS |
| | | | 10.50% | | PASS |
| | | | 8.50% | | PASS |
| | | | | 10.50% | Crystals F/T @ 10 days |
| 2.62% | | | 7.88% | | Crystals 5° C. @ 4 days |
| 1.50% | | | 9.0% | | Crystals F/T @ 8 days |
| | 2.62% | | 7.88% | | Crystals 5° C. @ 4 days |
| | | 2.62% | 7.88% | | PASS |
| | | 1.50% | 9.0% | | PASS |
| | | 2.62% | | 7.88% | PASS |
| | | 1.50% | | 9.0% | PASS |
| 5.25% | | | | 5.25% | Crystals 5° C. @ 4 days |
| | 5.25% | | | 5.25% | Crystals 5° C. @ 4 days |
| | | 5.25% | | 5.25% | PASS |
| | | | 5.25% | 5.25% | PASS |
| 7.88% | | | | 2.62% | Crystals 5° C. @ 4 days |
| | 7.88% | | | 2.62% | Crystals 5° C. @ 4 days |
| | | 7.88% | | 2.62% | PASS |
| | | | 7.88% | 2.62% | PASS |
| 7.88% | | 2.62% | | | Crystals 5° C. @ 4 days |
| | 7.88% | 2.62% | | | Crystals 5° C. @ 4 days |
| 7.88% | | | 2.62% | | Crystals 5° C. @ 4 days |
| 9.0% | | | 1.50% | | Crystals 5° C. @ 4 days |
| | 7.88% | | 2.62% | | Crystals 5° C. @ 4 days |
| | 9.0% | | 1.50% | | Crystals 5° C. @ 4 days |

As shown in Table 3, with the level of total active maintained at 22.5%, it was unexpectedly found that neither butylene or propylene glycol, alone or in combination with each other or dipropylene glycol, was suitable to maintain solubility of the actives at the upper end of the solubility of ascorbic acid in water. Failure was shown by the formation of visibly detectable crystals in the test composition. The compositions that passed did not show visibly detectable crystals. The results show that a glycol or combination of glycols selected from dipropylene glycol, pentylene glycol, hexylene glycol, a combination of dipropylene glycol and pentylene glycol, and a combination of dipropylene glycol and hexylene glycol, provide a composition that is stable (i.e., free of visibly detectable precipitate/crystals) in the presence of a high amount of actives in a range from 16% to 30% that include ascorbic acid at or near its solubility limit in water.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:
1. A hydroglycolic cosmetic composition comprising:
(a) a combination of skin actives comprising:
  (i) about 10% to about 30% ascorbic acid;
  (ii) a cinnamic acid derivative; and
  (iii) Vitamin E;
(b) a combination of glycols selected from the group consisting of:
  (i) a combination of pentylene glycol and dipropylene glycol present in a ratio that is in a range from about 1:6 to about 3:1 pentylene glycol to dipropylene glycol; and
  (ii) a combination of hexylene glycol and dipropylene glycol present in a ratio that is in a range from about 1:6 to about 3:1 hexylene glycol to dipropylene glycol;
(c) water in a range from about 40% up to about 75%; and
(d) at least one surfactant selected from the group consisting of polyoxyethylene sorbitan monolaurate, laureth-23, polyoxyethylene (80) sorbitan monooleate, and combinations thereof, all excluding esters, present in the composition in a range from about 1% to about 5%,
all amounts and ratios based on the weight of the composition,
wherein the composition demonstrates stability of solubility of the actives at temperatures in the range from about 5° C. to about 45° C. and at a pH that is in the range from about 3.0 to about 3.5, all over a time period of at least about 4 days, wherein the hydroglycolic cosmetic composition is free of lactobionic acid and is free of gluconolactone; and wherein the hydroglycolic cosmetic composition is free of polyphenols other than mangiferin, resveratrol, tannic acid, ferulic acid, chlorogenic acid, bioflavonoids, rosemary extracts, olive leaf extracts, or green tea extracts.

2. The hydroglycolic cosmetic composition according to claim 1, wherein the total amount of skin care actives present in the composition is in a range from about 16% to about 30%, based on the weight of the composition.

3. The hydroglycolic cosmetic composition according to claim 1, wherein the total amount of the combination of glycols present in the composition is in a range from at least about 10% to less than about 30%, all amounts and ratios based on the weight of the composition.

4. The hydroglycolic cosmetic composition according to claim 1, wherein the ascorbic acid is present in a ratio of water to ascorbic acid in a range from about 3:1 to about 10:1, based on the weight of the composition.

5. The hydroglycolic cosmetic composition according to claim 1, wherein the at least one surfactant is selected from the group consisting of the polyoxyethylene sorbitan monolaureate, the laureth-23, and combinations thereof.

6. The hydroglycolic cosmetic composition according to claim 1, wherein the at least one surfactant is present in the composition in a ratio of surfactant to Vitamin E in a range from about 2:1 to greater than 3:1, based on the weight of the composition.

7. The hydroglycolic cosmetic composition according to claim 1, wherein the cinnamic acid derivative is ferulic acid and wherein the Vitamin E is a tocopherol.

8. The hydroglycolic cosmetic composition according to claim 1, wherein the combination of skin actives further comprises a skin active selected from the group consisting of phytic acid, carnosine, chlorogenic acid, hyaluronic acid, panthenol, a sun filter, at least one hydroxy acid, and combinations thereof.

9. The hydroglycolic cosmetic composition according to claim 1, wherein the combination of skin actives further comprises a skin active selected from the group consisting of alpha, beta or polyhydroxy acids selected from the group consisting of lactic acid, glycolic acid, salicylic acid, malic acid, tartaric acid, citric acid, mandelic acid, galactose, and combinations thereof.

10. The hydroglycolic cosmetic composition according to claim 1, further comprising at least one oil, wherein the at least one surfactant is present in the composition in a ratio of surfactant to oil in a range from about 2:1 to greater than 3:1, based on the weight of the composition.

11. The hydroglycolic cosmetic composition according to claim 1, wherein the composition further includes one or more additives selected from fragrances, preservatives, antimicrobials, coloring materials, essential oils, citric acid, sodium citrate, sodium chloride, pH-adjusting agents, chelating, and combinations thereof, and is free or essentially free of powders and solid particles, and wherein the composition excludes propylene glycol and butylene glycol.

12. A hydroglycolic cosmetic composition comprising:
(a) a combination of skin actives comprising:
  (i) ascorbic acid present in the composition in a range from about 10% to about 30% and in a ratio of water to ascorbic acid in a range from about 3:1 to about 10:1, based on the weight of the composition;
  (ii) a cinnamic acid derivative; and
  (iii) Vitamin E;
(b) at least one surfactant selected from the group consisting of polyoxyethylene sorbitan monolaurate, laureth-23, polyoxyethylene (80) sorbitan monooleate, and combinations thereof, all excluding esters, present in the composition in a range from about 1% to about 5%;
(c) a combination of glycols selected from the group consisting of:
  (i) a combination of pentylene glycol and dipropylene glycol present in a ratio that is in a range from about 1:6 to about 3:1 pentylene glycol to dipropylene glycol; and
  (ii) a combination of hexylene glycol and dipropylene glycol present in a ratio that is in a range from about 1:6 to about 3:1 hexylene glycol to dipropylene glycol; and
(d) water in a range from about 40% up to about 75%,
wherein the hydroglycolic cosmetic composition is free of lactobionic acid and is free of gluconolactone,
wherein the total amount of the combination of glycols present in the composition is in a range from at least about 10% to less than about 30%, all amounts and ratios based on the weight of the composition,
wherein the composition demonstrates stability of solubility of the actives at temperatures in the range from about 5° C. to about 45° C. and at a pH that is in the range from about 3 to about 3.5 all over a time period of at least about 4 days, and
wherein the hydroglycolic cosmetic composition is free of polyphenols other than mangiferin, resveratrol, tannic acid, ferulic acid, chlorogenic acid, bioflavonoids, rosemary extracts, olive leaf extracts, or green tea extracts.

13. The hydroglycolic cosmetic composition according to claim 12, wherein the cinnamic acid derivatives comprises ferulic acid wherein the Vitamin E is a tocopherol, and wherein the total amount of skin care actives present in the composition is in a range from about 16% to about 30%, based on the weight of the composition.

14. The hydroglycolic cosmetic composition according to claim 12, wherein the combination of skin actives further comprises a skin active selected from the group consisting of phytic acid, carnosine, chlorogenic acid, hyaluronic acid, panthenol, a sun filter, at least one hydroxy acid, and combinations thereof, and wherein the composition excludes propylene glycol and butylene glycol.

15. The hydroglycolic cosmetic composition according to claim 12, wherein the combination of skin actives further comprises a skin active selected from the group consisting of alpha, beta or polyhydroxy acids selected from the group consisting of lactic acid, glycolic acid, salicylic acid, malic acid, tartaric acid, citric acid, mandelic acid, galactose, and combinations thereof.

16. A method for providing a hydroglycolic cosmetic cosmetic composition, the method comprising:
(a) providing a combination of skin actives comprising about 10% to about 30% ascorbic acid, a cinnamic acid derivative, and Vitamin E, and, optionally, one or a more skin active selected from the group consisting of phytic acid, carnosine, chlorogenic acid, hyaluronic acid, panthenol, a sun filter, at least one hydroxy acid, and combinations thereof;
(b) providing a combination of glycols selected from the group consisting of:
  (i) a combination of pentylene glycol and dipropylene glycol present in a ratio that is in a range from about 1:6 to about 3:1 pentylene glycol to dipropylene glycol; and (ii) a combination of hexylene glycol and dipropylene glycol present in a ratio that is in a range from about 1:6 to about 3:1 hexylene glycol to dipropylene glycol, wherein the total amount of the at least one or the combination of glycols present in the composition is in a range from at least about 10% to less than about 30%;

(c) providing water in a range from about 40% up to about 75%; and (d) providing, at least one surfactant selected from the group consisting of polyoxyethylene sorbitan monolaurate, laureth-23, polyoxyethylene (80) sorbitan monooleate, and combinations thereof, all excluding esters, present in the composition in a range from about 1% to about 5%, all preceding amounts and ratios based on the weight of the composition; and (e) optionally providing one or more additives selected from fragrances, preservatives, anti-microbials, coloring materials, essential oils, citric acid, sodium citrate, sodium chloride, pH-adjusting agents, chelating agents, and combinations thereof, and is free or essentially free of powders and solid particles; and (f) combining the a combination of skin actives and the combination of glycols and any optional additives to provide a composition wherein each of the skin actives in the at least one or combination of skin actives is solubilized in the composition, wherein the hydroglycolic cosmetic composition is free of lactobionic acid and is free of gluconolactone, and wherein the hydroglycolic cosmetic composition is free of polyphenols other than mangiferin, resveratrol, tannic acid, ferulic acid, chlorogenic acid, bioflavonoids, rosemary extracts, olive leaf extracts, or green tea extracts.

17. The method according to claim 16, wherein ascorbic acid is present in a ratio of water to ascorbic acid in a range from about 3:1 to about 10:1, the cinnamic acid derivative is ferulic acid, the Vitamin E is a tocopherol, wherein the at least one surfactant is present in the composition in ratio of surfactant to Vitamin E in a range from about 2:1 to greater than 3:1, and wherein the composition excludes propylene glycol and butylene glycol, all amounts and ratios based on the weight of the composition.

* * * * *